United States Patent [19]

Akhter et al.

[11] Patent Number: 4,678,606

[45] Date of Patent: Jul. 7, 1987

[54] LIQUID CLEANSING COMPOSITION

[75] Inventors: Lalarukh Akhter, Newcastle upon Tyne; Ronald E. Atkinson, Hexham, both of England; Dwight E. Wages, Wilbraham, Mass.; Harold H. Beyer, Montgomery, Ohio

[73] Assignee: The Procter & Gamble Company, Cincinnati, Ohio

[21] Appl. No.: 790,717

[22] Filed: Oct. 24, 1985

Related U.S. Application Data

[63] Continuation of Ser. No. 749,065, Jun. 26, 1985, abandoned.

[30] Foreign Application Priority Data

Jul. 3, 1984 [GB] United Kingdom ............... 8416884

[51] Int. Cl.$^4$ .......................... C11D 1/83; C11D 3/37
[52] U.S. Cl. ..................... 252/542; 252/173; 252/174.17; 252/174.23; 252/544; 252/547; 252/548; 252/550; 252/551; 252/559; 252/DIG. 2; 252/DIG. 14; 252/DIG. 5
[58] Field of Search .............. 252/174.17, 174.23, 252/550, 551, 559, 173, DIG. 2, DIG. 5, DIG. 14, 548, 547, 542, 544

[56] References Cited

U.S. PATENT DOCUMENTS

| 3,962,418 | 6/1976 | Birkofer | 424/70 |
|---|---|---|---|
| 4,061,062 | 12/1977 | Oberstar et al. | 252/547 |
| 4,330,438 | 5/1982 | Dierassi et al. | 252/552 |
| 4,364,837 | 12/1982 | Pader | 252/173 |
| 4,414,144 | 11/1983 | Liebowitz et al. | 252/548 |
| 4,472,297 | 9/1984 | Bolich et al. | 252/531 |
| 4,491,539 | 1/1985 | Hoskins et al. | 252/541 |
| 4,543,205 | 9/1985 | Contamin | 252/546 |
| 4,556,510 | 12/1985 | Holsopple | 252/547 |
| 4,556,993 | 1/1986 | Secemski et al. | 252/559 |
| 4,564,463 | 1/1986 | Secemski et al. | 252/174.17 |
| 4,576,744 | 3/1986 | Edwards et al. | 252/554 |
| 4,617,148 | 10/1986 | Shields | 252/547 |

FOREIGN PATENT DOCUMENTS 004695 1/1984 Japan.

OTHER PUBLICATIONS

"Polymers for Personal Care Products", Application Bulletin, Celanese Plastic & Specialties Co.

*Primary Examiner*—Prince E. Willis
*Attorney, Agent, or Firm*—Leonard Williamson; Ronald L. Hemingway; Richard C. Witte

[57] ABSTRACT

Aqueous liquid cleansing compositions comprise about 8% to 50% of primary surfactant selected from anionic, cationic, zwitterionic, amphoteric and semi-polar surfactants, from about 0.1% to 6% of $C_6$–$C_{13}$ alcohol ethoxylate and from about 0.1% to 2% of a water-soluble nonionic, cationic or mixed nonionic-cationic polymeric thickening agent, preferably guar gum or derivative thereof. The compositions have desirable foaming, product stability and skin feel characteristics.

19 Claims, No Drawings

LIQUID CLEANSING COMPOSITION

CROSS-REFERENCE TO RELATED APPLICATION

This is a continuation of application Ser. No. 749,065, filed June 26, 1985, now abandoned.

TECHNICAL FIELD

This invention relates to liquid cleansing compositions and, more specifically, to aqueous liquid cleansing compositions having desirable foaming, product solubility and skin feel characteristics.

BACKGROUND

Liquid cleansing products are extensively used as hand cleaners, shampoos, bath foams and for many other purposes. The present invention is concerned primarily with cleansers used for cleaning skin but is not limited to that application. The cleansers of interest are aqueous based and contain a mixture of surfactants.

In order to achieve controlled use of a liquid cleansing composition, it is desirable to have a somewhat viscous but pourable or pumpable product. A thin, watery product is too easily spilled and wasted when used and does not have good consumer acceptance. A number of high molecular weight polymeric materials have been used in a wide variety of aqueous based products in a thickening, gelling, suspending or protective colloid functionality. Certain nonionic polymers are also known to impart desirable skin feel characteristics to the product, notably guar gum and derivatives thereof (see EP-A-No. 67025). However, cleansing products formulated with the levels of surfactant and polymer necessary to provide satisfactory foaming, thickening and skin feel properties suffer from poor product solubility and viscosity characteristics, especially on storage at low temperatures. Moreover, the solubility and viscosity characteristics are further aggravated by the use of fatty acid alkanolamides which are customarily added to liquid cleansing compositions for suds-boosting purposes. These problems can be mitigated to some extent by adding substantial levels of alcoholic solvents such as ethanol and the like. Nevertheless, the resulting products are not only expensive but are technically undesirable because alcoholic solvents are believed to have a tendency to cause drying of the skin.

It has now been discovered that liquid cleansing products having desirable foaming, thickening and skin feel properties together with excellent formulation solubility and viscosity characteristics at both normal and low storage temperatures are provided by the use of polymeric thickening materials together with a mixed surfactant system comprising additive levels of specified nonionic ethoxylated aliphatic alcohols.

SUMMARY OF THE INVENTION

According to the present invention, therefore, there is provided an aqueous liquid cleansing composition comprising:

(a) from about 8% to about 50% of primary surfactant selected from anionic, cationic, zwitterionic, amphoteric and semi-polar surfactants and mixtures thereof, (b) from about 0.1% to about 6% of auxiliary surfactant selected from ethoxylated aliphatic alcohols having an average alkyl chain length of from 6 to 13 carbon atoms, (c) from about 0.1% to about 2% of a water-soluble polymeric thickening agent.

The water-soluble thickening agent useful in the present compositions can be a nonionic or cationic polymeric thickening agent or a mixture thereof. Preferred nonionic water-soluble polymers are selected from guar gum, hydroxypropyl guar gum, methyl cellulose, methyl hydroxypropyl cellulose, hydroxyethyl cellulose, hydroxypropyl cellulose, locust bean gum, starch, starch amylose, hydroxyethylamylose and polyoxyethylene. The polymer is a high molecular weight material (mass-average molecular weight being generally from about 50,000 to about 5,000,000, preferably from about 100,000 to about 1,000,000), and its thickening ability is preferably such that a 1% dispersion of the polymer in water at 20° C. exceeds about 20 Pa.s (200 poise) at a shear rate of $10^{-2}$ sec$^{-1}$.

Highly preferred polymers herein are guar gum and derivatives thereof which provide a highly desirable smooth slippery skin feel to the products. Guar gum is a naturally occurring material which is the principal component of the seed of the guar plant. Guar gum is extracted from the guar seed and purified. Guar gum is a high molecular weight carbohydrate polymer or polysaccaride made up of mannose and galactose units linked together. The guar molecule is essentially a straight chain of mannose units linked to each other by means of beta (1-4) glycosidic linkages. Galactose units branch from alternate mannose units through alpha (1-6) linkages with the mannose units.

The desired skin feel of the liquid cleansing products is preferably obtained by using hydroxypropyl guar gum. In the guar gum molecule, each mannose and galactose unit has from 2-4 hydroxyl groups, depending on where the units are located in the polymer chain. Guar gum derivatives are produced by reacting guar gum such that substitution of chemical moieties occurs on some of these hydroxyl groups. Hydroxypropyl guar gums are a family of materials with hydroxypropyl groups substituted for some of the hydroxyl groups. The term "degree of substitution" is used to indicate the average number of hydroxypropyl groups which occur on each of the sugar units in the polymer molecule. The preferred hydroxypropyl guar gum used in the present invention has a degree of substitution of from about 0.3 to 1.2; especially preferred is hydroxypropyl guar gum with a degree of substitution of about 0.6. Such a material is available commercially as Jaguar HP-60 from Meyhall Chemical Ltd.

Preferred cationic polymeric thickening agents herein are selected from hydroxypropyltrimethylammonium guar gums, quaternized cellulose ethers, homopolymers of dimethyl diallyl ammonium chloride, copolymers of dimethyl diallyl ammonium chloride and acrylamide, quaternized vinyl pyrrolidone acrylate or methacrylate copolymers of amino alcohol, and polyalkylene imines, in particular the polyethylene imines and the ethoxy polyalkylene imines. Of these, highly preferred are hydroxypropyl trimethyl ammonium guar gum, quaternized cellulose ethers and mixtures thereof. Mixtures of the above specified cationic and nonionic thickening agents are also suitable herein.

By way of exemplification, cationic polymers preferred for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM), and also Jaguar C-16(RTM), which contains hydroxypropyl substituents (d.s. of from 0.8–1.1) in addition to the above-specified cationic groups, and quaternized cellulose ethers available commercially under the trade names Ucare Polymer JR and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide available commercially under the trade names Merquat 550 and Merquat S, quaternized vinyl pyrrolidone acrylate or methacrylate copolymers of amino alcohol available commercially under the trade name Gafquat, and polyalkyleneimines such as polyethylenimime and ethoxylated polyethylenimine.

The quantity of polymer material used in the liquid cleansing products of this invention is from about 0.1% to about 2%, especially from about 0.2% to about 1%. A preferred range of usage for guar gum and its derivatives is from about 0.3% to about 0.7%.

The liquid cleansing compositions of this invention comprise a primary surfactant selected from anionic, cationic, zwitterionic and amphoteric surfactants and mixtures thereof, together with an auxiliary surfactant which is a specific type of nonionic surfactant material. The primary surfactant comprises from about 8% to about 50%, preferably from about 10% to about 30%, more preferably from about 15% to about 25% by weight of the composition; the auxiliary surfactant comprises from about 0.1% to about 6%, preferably from about 0.5% to about 4%, more preferably from about 1% to about 3% by weight of the composition.

Suitable anionic surfactants are water-soluble salts of $C_8$–$C_{22}$ alkyl benzene sulphonates, $C_8$–$C_{22}$ alkyl sulphates, $C_{10\text{-}18}$ alkyl polyethoxy ether sulphates, $C_{8\text{-}24}$ paraffin sulphonates, alpha-$C_{12\text{-}24}$ olefin sulphonates, alpha-sulphonated $C_6$–$C_{20}$ fatty acids and their esters, $C_{10}$–$C_{18}$ alkyl glyceryl ether sulphonates, fatty acid monoglyceride sulphates and sulphonates, especially those prepared from coconut oil, $C_8$–$C_{12}$ alkyl phenol polyethoxy ether sulphates, 2-acyloxy $C_9$–$C_{23}$ alkane-1-sulphonate, and beta-alkyloxy $C_8$–$C_{20}$ alkane sulphonates.

Preferably, the anionic surfactant is selected from alkali metal, alkaline earth metal, ammonium, and alkanolammonium salts of alkyl sulphates, alkyl ethoxy sulphates, alkyl benzene sulphonates and mixtures thereof.

The alkyl sulphate component is preferably a primary alkyl sulphate in which the alkyl group contains about 10–16 carbon atoms, more preferably an average of 12–14 carbon atoms. The alkyl group may be linear or branched in configuration. $C_{10}$–$C_{16}$ alcohols, derived from natural fats or Ziegler olefin build-up or OXO synthesis, form suitable sources for the alkyl group. Examples of synthetically derived materials include Dobanol 23 (RTM) sold by Shell Chemicals (UK) Ltd, Ethyl 24 sold by the Ethyl Corporation, a blend of $C_{13}$–$C_{15}$ alcohols in the ratio 67% $C_{13}$, 33% $C_{15}$ sold under the trade name Lutensol by BASF GmbH and Synperonic (RTM) by ICI Ltd, and Lial 125 sold by Liquichimica Italiana. Examples of naturally occurring materials from which the alcohols can be derived are coconut oil and palm kernel oil and the corresponding fatty acids.

The level of the alkyl sulphate component generally lies in the range of from about 4% to about 20% by weight of the composition, more generally from about 4% to about 16% by weight. In one preferred compositional aspect of the invention in which alkyl benzene sulphonate is also incorporated, the usage level lies in the range from about 8% to about 12% by weight, most preferably in the range from about 8% to about 11% by weight. In another compositional aspect of the invention in which a sulphonate component is not present, the alkyl sulphate level lies in the range from about 12% to about 20%, more preferably from about 14% to about 18% by weight.

For the purposes of the present invention any alkali metal, alkaline earth metal, ammonium or substituted ammonium cation can be used in association with the alkyl sulphate. In particular, the alkyl sulphate can be associated with a source of magnesium ions either introduced as the oxide or hydroxide to neutralise the acid, or added to the composition as a water soluble salt. In practice the magnesium ion will be present at a level of from about 0.001% to about 0.70% by weight, preferably from 0.01% to 0.1% by weight of the composition.

Alkyl benzene sulphonates preferred for use in compositions of the present invention are those in which the alkyl group, which is substantially linear, contains about 10–16 carbon atoms, preferably about 11–13 carbon atoms, a material with an average chain length of 11.8 being most preferred. An alkylbenzene sulphonate content of from about 10% to about 28% by weight of the composition is generally suitable. In a preferred aspect of the invention an alkylbenzene sulphonate content of from 13% to 17% by weight is used.

The alkyl ethoxy sulphate surfactant component preferably comprises a primary alkyl ethoxy sulphate derived from the condensation product of a $C_{10}$–$C_{16}$ alcohol with an average of up to 6 ethylene oxide groups. The $C_{10}$–$C_{16}$ alcohol itself can be obtained from any of the sources previously described for the alkyl sulphate component. It has, however, been found preferable to use alkyl sulphate and alkyl ether sulphate in which the carbon chain length distributions are the same. $C_{12}$–$C_{13}$ alkyl ether sulphates are preferred and the level of alkyl ethoxy sulphate in the composition lies generally between about 8% and about 25% by weight of the compositions. In compositions additionally incorporating an alkyl benzene sulphonate surfactant, the level of alkyl ethoxy sulphate generally lies in the range from 9% to 15% by weight.

Conventional ethoxylation processes result in a distribution of individual ethoxylates ranging from 1 to about 10 ethoxy groups per mole of alcohol, so that the desired average can be obtained in a variety of ways. Blends can be made of material having different degrees of ethoxylation and/or different ethoxylate distributions arising from the specific ethoxylation techniques employed and subsequent processing steps such as distillation. For example, it has been found that approximately equivalent sudsing to that given by a blend of alkyl sulfate and alkyl triethoxy ether sulfate can be obtained by reducing the level of alkyl sulfate and using an alkyl ether sulfate with an average of approximately two ethoxy groups per mole of alcohol. In preferred compositions in accordance with the present invention the average degree of ethoxylation is from about 0.5 to about 4, more preferably from about 0.8 to about 2.0.

Cationic detergents include those having the formula $R-N(R^2)_3^{(+)}X^{(-)}$ wherein R is an alkyl chain containing from about 8 to about 20 carbon atoms, each $R^2$ is selected from alkyl and alkanol groups containing from 1 to 4 carbon atoms and benzyl groups, there being normally no more than one benzyl group and two $R^2$ groups can be joined by either a carbon-carbon ether, or imino linkage to form a ring structure, and X represents a halogen atom, sulfate group, nitrate group or other pseudohalogen group. Specific examples are coconut alkyl trimethyl ammonium chloride, dodecyldimethyl benzyl bromide and dodecyl methyl morpholino chloride.

Zwitterionic synthetic detergents can be broadly described as derivatives of aliphatic quaternary ammonium, phosphonium, and sulfonium compounds, in which the aliphatic radical may be straight chain or branched, and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are 3-(N,N-dimethyl-N-hexadecylammonio)propane-1-sulfonate and 3-(N,N-dimethyl-N-hexadecylammonio)-2-hydroxy propane-1-sulfonate.

Amphoteric synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are sodium-3-dodecylaminopropionate and sodium-3-dodecylaminopropane sulfonate.

Other suitable primary surfactants herein are the long chain tertiary amine oxides of general formula

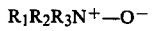

$$R_1R_2R_3N^+ - O^-$$

wherein $R_1$ represents alkyl, alkenyl or monohydroxy alkyl radical of from 8 to 18 carbon atoms optionally containing up to 10 ethylene oxide moieties or a glyceryl moiety, and $R_2$ and $R_3$ represents alkyl of from 1 to 3 carbon atoms optionally substituted with a hydroxy group, e.g., methyl, ethyl, propyl, hydroxy ethyl, or hydroxy propyl radicals. Examples include dimethyldodecylamine oxide, oleyldi(2-hydroxyethyl)amine oxide, dimethyloctylamine oxide, dimethyltetradecylamine oxide, dimethyldecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)-amine oxide, dimethylhexadecylamine oxide. The amine oxide surfactants are generally referred to as semi-polar although in acid to neutral media they behave akin to cationic surfactants.

The auxiliary surfactant component of the invention is a $C_6-C_{13}$ aliphatic alcohol ethoxylate generally containing an average ($E_{av}$) of from about 1.5 to about 25, preferably from about 2 to 15 and more preferably from about 6 to about 10 moles of ethylene oxide per mole of alcohol. The auxiliary surfactant preferably contains not more than about 1% by weight of unethoxylated alcohol when the ethoxylated alcohol contains an average of less than 9 moles of ethylene oxide and not more than about 2% by weight of unethoxylated alcohol when the ethoxylated alcohol contains an average of 9 or more moles of ethylene oxide per mole of alcohol. Such surfactants are preferred from the viewpoint of low temperature stability, the unethoxylated content preferably being less than about 0.7%, and more preferably less than about 0.5%. The unethoxylated material can be removed by vacuum distillation.

The starting alcohol may be a primary or secondary alcohol but is preferably a primary alcohol which may be derived from natural or synthetic sources. Thus natural fats or oils, or products of Zeigler olefin build up reactions or OXO synthesis may all be used as the source of the hydrocarbon chain, the structure of which may be linear or branched in type.

The preferred alcohol chain length range is from $C_9-C_{11}$ as it has been found that sudsing performance is optimum for ethoxylates made from such alcohols. It is also desirable for performance reasons that the hydrophilic-lipophilic balance (HLB) of the ethoxylated alcohol is in the range from 8.0 to 17.0, more preferably from 11.0 to 17.0 and most preferably from 11.0 to 15.0.

An optional but preferred ingredient of the compositions herein is from about 0.1% to about 10%, preferably from about 0.1% to about 6%, more preferably from about 1% to about 5% of a polyoxy($C_2-C_3$)alkylene glycol having an average molecular weight in the range from about 200 to about 15,000, preferably from about 300 to about 6000. Suitable materials herein include polyoxyethyleneglycol, polyoxypropyleneglycol, block copolymers of polyoxyethyleneglycol and polyoxypropyleneglycol and mixtures thereof. A highly preferred material is polyoxyethylene glycol 6000. In particular, the combined use of the auxiliary nonionic surfactant and polyoxyethyleneglycol is found herein to be particularly valuable for achieving optimum product stability, pourability and solubility in aqueous liquors. In general, the compositions of the invention contain a strong acid-derived electrolyte level of less than about 0.5%, preferably less than about 0.1% for optimum product stability.

In general, the compositions herein have a viscosity (neat) at 24° C. in the range from about 1,000 to about 20,000 cps, preferably from about 2,000 to about 15,000 cps, more preferably from about 4,000 to about 12,000 cps, viscosity being measured in a Brookfield LVT viscometer using spindle number 4 at speed 3.

Although the addition of fatty acid alkanolamides (e.g. $C_{10}-C_{16}$ mono- and di-$C_2-C_3$ alkanolamides) in higher levels has a generally deleterious effect on formulation physical characteristics, nevertheless such materials can be added for additional suds-boosting effect and thickening effect provided the amide is maintained at low concentration in product, preferably no more than about 4% by weight.

In the same way, it is a feature of the invention that the compositions require no or reduced levels of low molecular weight organic solvent (mol. wt. less than 150) for satisfactory product stability, and desirably such solvents are added in levels such that the total solvent (i.e. lower organic solvent+polyoxyalkyleneglycol) is from about 0.1% to about 20%, preferably from about 0.1% to about 10%, more preferably from about 1% to about 6% by weight of composition. If appropriate, however, a material such as ethylene glycol or propylene glycol can be added for a solvent function.

Where the composition of a liquid cleansing product will be in contact with the skin of the users, it is preferred that the cleansing product be formulated to provide a pH in use within the range of from about 4 to about 10, depending upon the particular surfactant or materials employed. Especially preferred is a pH in the range of 5 to 7. Any of a large number of known substances can be used to adjust the pH of the liquid cleansing product, e.g., sodium hydroxide, citric acid, generally at a level of up to about 0.5% of the product composition.

Perfumes may be used in formulating the liquid cleansing products, generally at a level of about 0.1% to about 5% of the product composition. Colorants may also be used in the liquid cleansing products. Opacifiers, e.g., ethylene glycol distearate, polystyrene latex, generally at a level of about 0.2% to about 2.0% of the product composition, may be used in the liquid cleansing products to provide them with an opaque or pearlescent appearance. Preservatives, e.g., EDTA, methyl paraben, propyl paraben, Germall 115, Kathon, generally at a level of less than 1%, may be incorporated in the liquid cleansing products to prevent microbiological growth in the products.

The liquid cleansing products of the present invention contain at least about 42% water, preferably from about 60% to about 90% water.

The invention is illustrated in the following non-limitative examples in which all parts and percentages are by weight unless otherwise specified:

| Examples I to VI | I | II | III | IV | V | VI |
| --- | --- | --- | --- | --- | --- | --- |
| Sodium $C_{12-13}$ alkyl sulphate | 8 | 9 | 5 | 6 | 8 | — |
| Sodium $C_{12-13}$ (EO)$_2$ alkyl sulphate | 12 | — | — | — | 8 | — |
| Sodium $C_{12-13}$ (EO)$_3$ alkyl sulphate | — | 11 | 8 | 6 | — | — |
| Ammonium $C_{12-13}$ (EO)$_3$ alkyl sulphate | — | — | — | — | — | 20 |
| Commercial $C_{10}$ alcohol (EO)$_{10}$ | 4 | 2 | — | 3 | — | 2 |
| Commercial $C_{9-11}$ alcohol (EO)$_5$ | — | — | 4 | — | 2 | — |
| Dodecyl dimethylamine oxide | — | — | — | — | — | 3 |
| Jaguar A-40-F[1] | — | — | — | 0.3 | — | — |
| Jaguar HP-60 | 0.4 | 0.6 | 0.3 | — | 0.5 | 0.55 |
| Propylene Glycol | 2 | — | — | — | 1 | — |
| Polyoxyethylene/polyoxypropylene block copolymer (Pluronic L-92) | — | — | — | — | — | 0.5 |
| Polyoxyethylene glycol 600 | 2 | 4 | 3 | 2 | 3 | — |
| Coconut Monoethanolamide | 2 | 2 | — | — | 1 | — |
| Ethyleneglycol distearate | 1 | 1 | 0.5 | 0.5 | 1 | 0.5 |
| Perfume | 4 | 3 | 3 | 3 | 2 | 2 |
| Preservative[2] | 0.3 | 0.4 | 0.3 | 0.4 | 0.3 | 0.25 |
| Citric acid | 0.2 | 0.3 | 0.3 | 0.2 | 0.3 | 0.3 |
| Magnesium chloride - 6H$_2$O | — | — | — | 0.1 | — | — |
| Dyes | 0.1 | 0.1 | 0.1 | 0.1 | 0.1 | 0.01 |

[1]Purified guar gum from Celanese Plastics & Specialties Company.
[2]Comprises Germal 115, Methyl Paraben, Propyl Paraben and ethylenediamine tetraacetic acid.

The above products are made by a batch process involving addition of a hot premix to a main mix in the following manner.

Hot Premix

A portion of the alkyl sulphate (supplied as a 28% aqueous solution) is heated in a premix tank to about 60° C. and the fatty alcohol ethoxylate and half the propylene glycol or polyoxyethylene glycol solvent are added thereto with agitation and heating to maintain a temperature of about 60° C. The preservative is then added and the premix is heated to about 65° C. at which temperature coconut monoethanolamide, if present, is added. Ethyleneglycoldistearate is added after further heating to a temperature of about 65° C. to 70° C.

Main Mix

The alkyl ether sulphate (supplied as a 28% active) and the remaining alkyl sulphate are added to a main mix tank together with the remaining water, if any. The guar material is then dispersed in the remaining propylene glycol or polyoxyethylene glycol and this is added to the main mix at ambient temperature. Finally the citric acid, and magnesium chloride, if present, are added.

The premix is then added with agitation at a temperature of about 70° C. to the main mix, the combined mixture is rapidly cooled in a heat exchanger and dyes and perfume are added to form the finished product.

In the case of Example VI, the process is repeated with the amine oxide, Pluronic L-92 and a portion of the alkyl ether sulphate being incorporated in the hot premix and with the remaining alkyl ether sulphate being incorporated into the main mix.

The resulting products have desirable foaming, thickening and skin feel properties together with excellent formulation solubility and viscosity characteristics at both normal and low storage temperatures.

What is claimed is:

1. An aqueous, liquid personal cleansing composition consisting essentially of:
   (a) from about 8% to about 50% of primary surfactant selected from the group consisting of anionic, cationic, zwitterionic, amphoteric and semi-polar surfactants and mixtures thereof,
   (b) from about 0.1% to about 6% of auxiliary surfactant selected from ethoxylated aliphatic alcohols having an average alkyl chain length of from 6 to 13 carbon atoms,
   (c) from about 0.1% to about 2% of a water-soluble polymeric thickening agent; wherein the thickening agent is selected from the group consisting of nonionic: guar gum, hydroxypropyl guar gum, methyl cellulose, methyl hydroxypropyl cellulose, hydroxypropyl cellulose, locust bean gum, starch, starch amylose, hydroxyethylamylose and polyoxyethylene; and cationic; hydroxypropyltrimethylammonium guar gums, quaternized cellulose ethers, homopolymers of dimethyl diallyl ammonium chloride, co-polymers of dimethyl diallyl ammonium chloride and acrylamide, quaternized vinyl pyrrolidone acrylate or methacrylate copolymers of amino alcohol, and polyalkylene imines, and mixtures thereof; and
   (d) from about 0.1% to about 10% of polyoxy($C_2$–$C_3$)alkyleneglycol having an average molecular weight in the range from about 200 to about 15,000.

2. A composition according to claim 1 wherein the thickening agent is a nonionic polymer selected from the group consisting of guar gum, hydroxypropyl guar gum, methyl cellulose, methyl hydroxypropyl cellulose, hydroxypropyl cellulose, locust bean gum, starch, starch amylose, hydroxyethylamylose and polyoxyethylene and mixtures thereof.

3. A composition according to claim 2 wherein the thickening agent is selected from guar gum and hydroxypropyl guar gum and mixtures thereof.

4. A composition according to claim 3 wherein the thickening agent is hydroxypropyl guar gum having a degree of substitution of from about 0.3 to about 1.2, preferably about 0.6.

5. A composition according to claim 1 wherein the primary surfactant is an anionic surfactant selected from the group consisting of alkali metal, alkaline earth metal, ammonium and alkanolammonium salts of $C_{10}$–$C_{16}$ alkyl sulphates, $C_{1-16}$ alkyl ethoxy sulphates containing up to about 6 molar proportions of ethylene oxide, $C_{10-16}$ alkyl benzene sulphonates and mixtures thereof.

6. A composition according to claim 1 wherein the aliphatic alcohol has an average alkyl chain length of from about 9 to about 11 carbon atoms.

7. A composition according to claim 6 wherein the aliphatic alcohol contains an average ($E_{av}$) of from about 2 to about 15 moles of ethylene oxide per mole of alcohol.

8. A composition according to claim 7 wherein the aliphatic alcohol contains an average ($E_{av}$) of from about 6 to about 10 moles of ethylene oxide per mole of alcohol.

9. A composition according to claim 7 wherein the auxiliary surfactant contains less than about 1% of unethoxylated aliphatic alcohol when $E_{av}$ is less than 9 and less than about 2% of unethoxylated alcohol when $E_{av}$ is equal to or greater than 9.

10. A composition according to claim 6 wherein the thickening agent is selected from guar gum and hydroxypropyl guar gum and mixtures thereof.

11. A composition according to claim 1 comprising from about 10% to about 30% of primary surfactant, from about 0.5% to about 4% of auxiliary surfactant, and from about 0.3% to about 0.7% of guar gum or hydroxypropyl guar gum.

12. A composition according to claim 1 additionally comprising from about 0.1% to about 6% of polyoxy($C_2$-$C_3$)alkyleneglycol having an average molecular weight in the range from about 200 to about 15,000.

13. A composition according to claim 1 wherein the polyoxy($C_2$-$C_3$)alkylene glycol is polyoxyethylene glycol having a molecular weight of about 600.

14. A composition according to claim 1 wherein the thickening agent is selected from guar gum and hydroxypropyl guar gum and mixtures thereof.

15. A composition according to claim 1 additionally containing from about 0.5% to about 4% of $C_{10}$-$C_{16}$ mono- or di-$C_2$-$C_3$ alkanolamide.

16. A composition according to claim 1 additionally comprising from about 0.1% to about 20% by weight of organic solvent selected from ethylene glycol, propylene glycol, polyoxyethylene glycol, polyoxypropylene glycol, block copolymers of polyoxyethylene glycol and polyoxypropylene glycol and mixtures thereof.

17. A composition according to claim 16 additionally containing from about 0.5% to about 4% of $C_{10}$-$C_{16}$ mono- or di-$C_2$-$C_3$ alkanolamide.

18. A composition according to claim 1 wherein the thickening agent is a cationic polymer selected from the group consisting of hydroxypropyltrimethylammonium guar gums, quaternized cellulose ethers, homopolymers of dimethyl diallyl ammonium chloride, co-polymers of dimethyl diallyl ammonium chloride and acrylamide, quaternized vinyl pyrrolidone acrylate or methacrylate copolymers of amino alcohol, and polyalkylene imines.

19. A composition according to claim 18 wherein the thickening agent is selected from hydroxypropyl trimethylammonium guar gum, quaternized cellulose ethers and mixtures thereof.

* * * * *

UNITED STATES PATENT AND TRADEMARK OFFICE
CERTIFICATE OF CORRECTION

PATENT NO. : 4,678,606
DATED : July 7, 1987
INVENTOR(S) : Lalarukh Akhter, Ronald E. Atkinson, Dwight E. Wages and Harold H. Beyer It is certified that error appears in the above-identified patent and that said Letters Patent is hereby corrected as shown below:

IN THE CLAIMS:

Col. 8, line 67, (Claim 5) "$C_{1-16}$" should read -- $C_{10}-C_{16}$ --.

Signed and Sealed this

Third Day of May, 1988

Attest:

DONALD J. QUIGG

Attesting Officer

Commissioner of Patents and Trademarks